United States Patent

Leight

[11] Patent Number: 5,372,278
[45] Date of Patent: Dec. 13, 1994

[54] EARPLUG DISPENSER BOX

[76] Inventor: Howard S. Leight, 1330 Colorado Ave., Santa Monica, Calif. 90404

[21] Appl. No.: 55,266

[22] Filed: Apr. 27, 1993

[51] Int. Cl.$^5$ .............................................. B23Q 7/00
[52] U.S. Cl. .................... 221/174; 221/197; 229/122.2
[58] Field of Search ............... 221/287, 174, 176, 197, 221/305, 167, 49; 229/122.2, 23 R, 125.39, 127; 312/42, 35; 220/318, 324

[56] References Cited

U.S. PATENT DOCUMENTS

| | | | |
|---|---|---|---|
| 1,753,957 | 4/1930 | Washburn | 221/287 |
| 2,032,880 | 3/1936 | Kinsley et al. | 229/125.39 |
| 2,113,481 | 4/1938 | Kasdorf | 229/125.39 |
| 2,645,408 | 7/1953 | Eckles | 229/125.39 |
| 3,799,409 | 3/1974 | Goerke | 229/122.2 |
| 4,759,469 | 7/1988 | Lowrance et al. | 221/197 |
| 4,767,022 | 8/1988 | Oldorf | 221/197 |
| 4,793,549 | 12/1988 | Wald | 229/125.39 |
| 4,846,345 | 7/1989 | Hamuro et al. | 221/174 |

Primary Examiner—Kenneth W. Noland
Attorney, Agent, or Firm—Arthur Freilich; Robert D. Hornbaker; Leon D. Rosen

[57] ABSTRACT

A container is described which can hold multiple small articles such as earplugs, and which can be inserted into a dispenser where the contents can be readily released. The container includes a box (30, FIG. 3) whose bottom wall includes a pair of flaps (50, 52) having inner ends (54, 56) pivotally connected to the bottoms of opposite side walls, and having outer portions (64, 66) that lie adjacent to each other. A release device (34) holds the outer portions of the flaps together to prevent them from pivoting down until the release device is pulled out, when the flaps pivot down and the articles fall out. The outer portion of each flap includes an upstanding tab (76, 78, FIG. 5) with a horizontal slot (82), and the release device includes a cardboard plate which is received in the slot. While the upper walls (84) of the slots press down against the release plate, the widely spaced opposite sides (90, 92) of the release plate bear against the upper surfaces (94, 96) of the flaps to prevent the tabs (76, 78) and therefore the flaps (50, 52) from moving down.

15 Claims, 5 Drawing Sheets

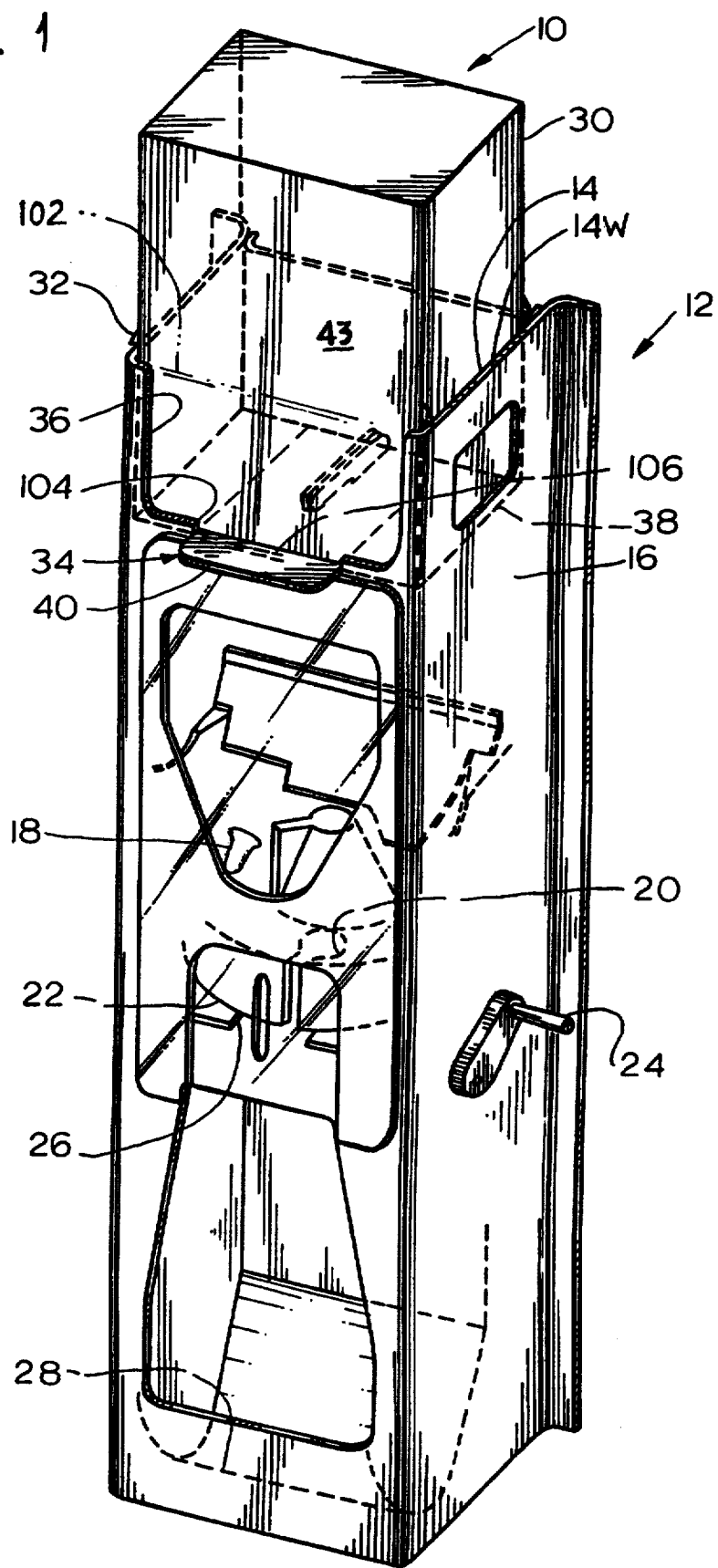

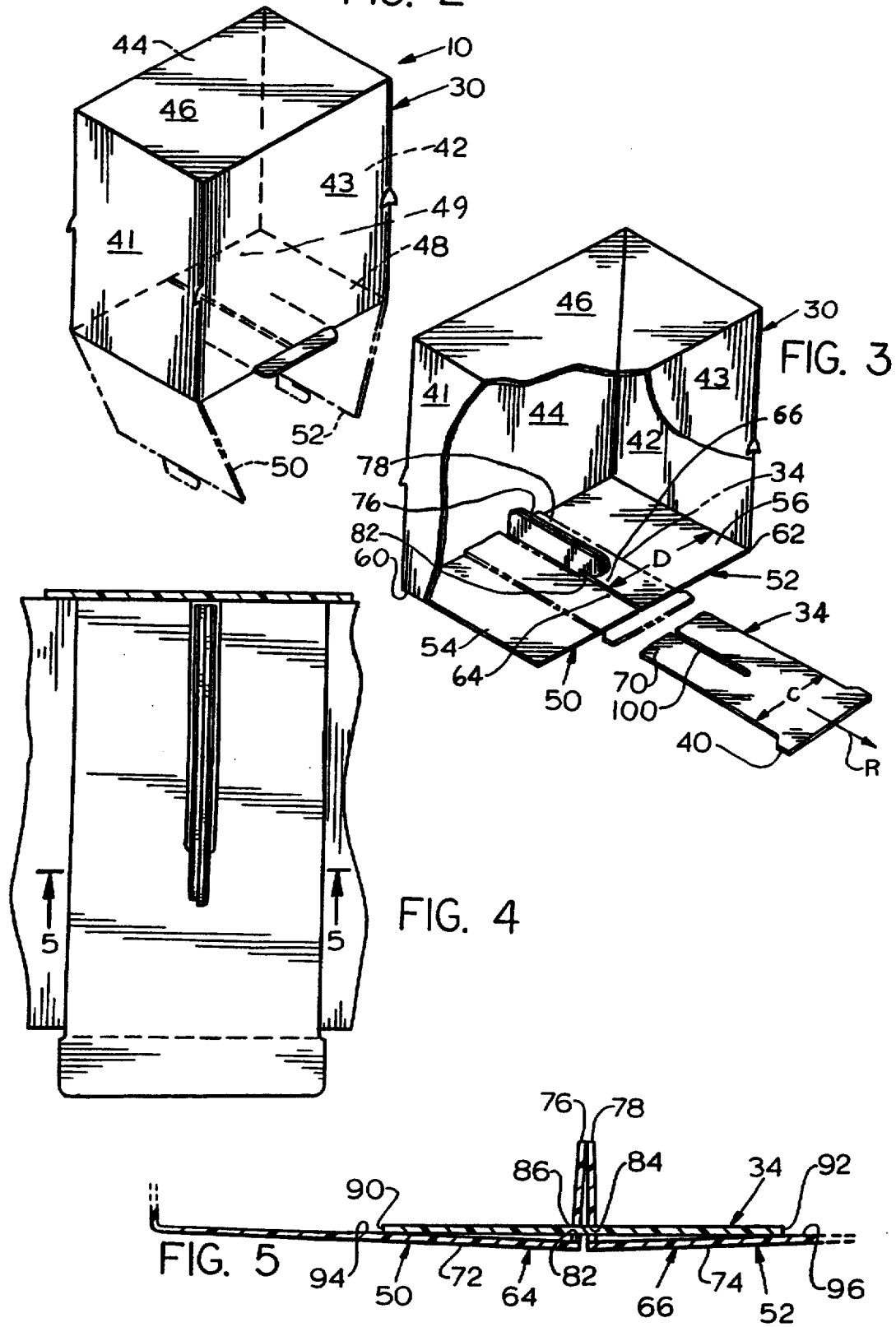

EARPLUG DISPENSER BOX

BACKGROUND OF THE INVENTION

Disposable earplugs, which each have a length of about one inch and a diameter of about 0.5 inch, can be conveniently packaged in cardboard boxes that each hold several hundred, for shipment to a factory. At the factory, the contents of a box can be emptied into a dispenser which dispenses one or two earplugs at a time. The contents of prior art boxes are commonly removed by opening the top of a box and removing the contents by grabbing perhaps a couple of dozen earplugs at a time. Another method is to open the top of the box and tip the box to pour out the contents. Both of these methods can lead to loss of some earplugs. A worker who grabs a bunch at a time from a box may have dirty hands, so he may soil some earplugs and workers may not wish to use them, or he may drop some earplugs on the floor where they are dirtied and become nonuseable. Pouring of the earplugs can also lead to many earplugs spilling onto the ground. A box that could be readily emptied into a dispenser or other receiver, without requiring direct contact with human hands, and without substantial danger of spillage, would be useful in the emptying of boxes of earplugs, as well as other articles of comparable size. Comparable size relates to articles that are not so small (e.g. less than about one sixteenth inch minimum dimensions) so they can fall out of thin slits in a box, but which are small enough so that a multiplicity (e.g. at least seven) articles can be contained in a single box.

SUMMARY OF THE INVENTION

In accordance with one embodiment of the present invention, a container is provided which can readily release multiple small articles held therein, into a receiver such as a dispenser, without involving handling by human hands and without substantial danger of spillage. The container includes a box with a bottom wall that has at least one flap. The flap has an inner end pivotally mounted at the bottom of a side wall of the box, and has a free outer end portion. A release device has an inner part coupled to the outer flap portion and to another portion of the box, to support the outer portion of the flap on another portion of the box, until the release device is pulled out to release the flap and allow it to pivot down under the weight of articles in the box.

The bottom wall of the box can include two flaps having inner ends pivotally connected to opposite side walls of the box, and having adjacent outer end portions. Each flap outer end portion has a tab forming a slot with an upper slot wall. The release device can be in the form of a plate whose inner portion lies in the slot to support the tabs, with widely spaced opposite sides of the plate supported on upper surfaces of the flaps.

A plate-like release device can have an outer end forming a handle that normally projects from the side of the box, but which can bend upwardly. This enables the box to be inserted into an open top of a dispenser or the like which closely receives the box. The box can be pushed down until the handle reaches a dispenser opening through which the handle is accessible, to be grasped and pulled out. The box can be formed of a single sheet of cardboard, with cuts near the vertical corners of the box that form stops that can abut the top of a dispenser or the like to determine how deep the box is inserted into the dispenser.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric and partially broken-away view of an earplug dispenser, showing a container of the present invention installed thereon, with the release device ready to be released.

FIG. 2 is an isometric view of the container of FIG. 1 in a closed configuration and also showing in phantom lines, the bottom flaps in an open configuration.

FIG. 3 is a view similar to that of FIG. 2, but with part of the box top and side walls broken away, and with the release device shown in solid lines in the release position and in phantom lines in the retain position.

FIG. 4 is a partial plan view of the release device and of a portion of the bottom wall flaps of FIG. 3.

FIG. 5 is a view taken on the line 5—5 of FIG. 4.

DESCRIPTION OF THE PREFERRED EMBODIMENTS

Figure 6:
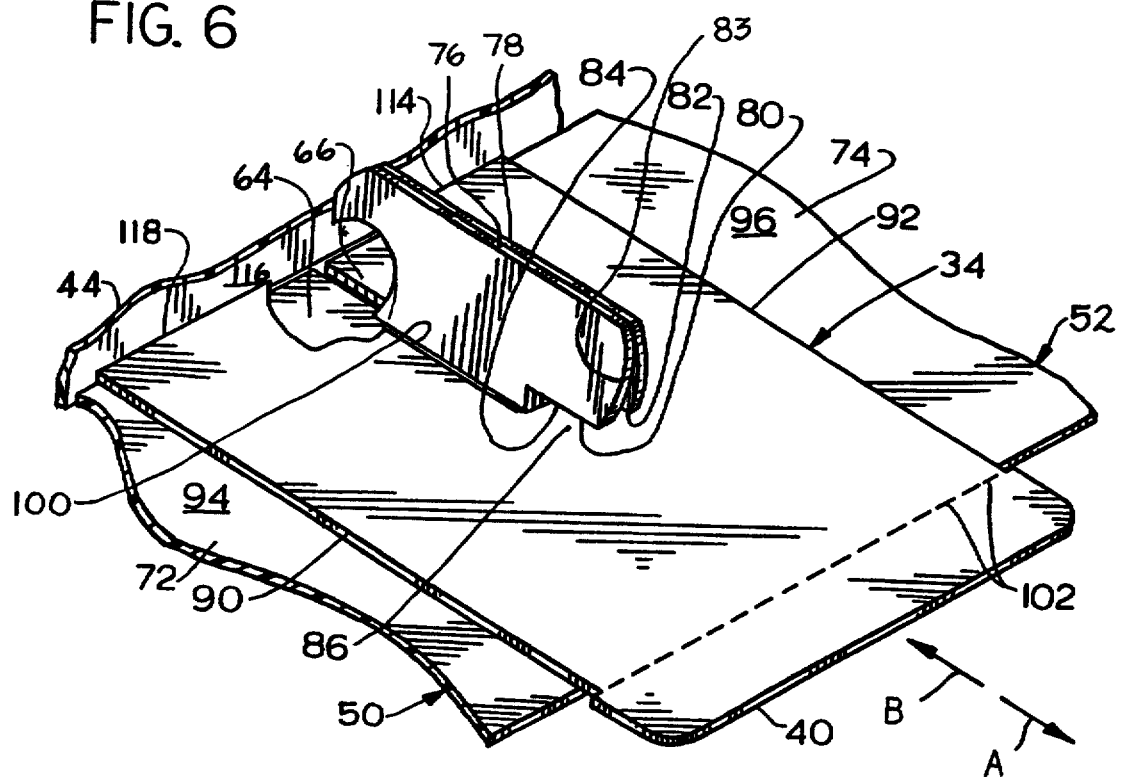
FIG. 6 is a partial isometric view of the apparatus of FIG. 4.

FIG. 1 illustrates a container 10 of the present invention, which is filled with earplugs and which is shown installed on an earplug dispenser 12. The earplug dispenser has an open top 14 for receiving the container, and has a frame 16 that forms a hopper for receiving earplugs. One of the earplugs is indicated at 18. The earplugs fall into holes 20 of a wheel 22 that turns when a crank 24 is turned, to bring each hole and a corresponding earplug therein to a location over a dispense passage 26. The earplug drops out of the hole through the dispense passage, into a workman's hand or into a receiver 28 from which earplugs are removed. A workman commonly turns the wheel until two earplugs have been dispensed. An industrial workplace may have many oil or grease-covered surfaces, and workmen are asked to clean their hands before touching the earplugs. However, some workmen will have dirty hands. The container 10 and dispenser 12 are constructed so that a person can load the earplugs initially held in the container into the dispenser and can operate the dispenser to dispense a pair of earplugs, without having any worker's hands (which may be dirty) touch the earplugs.

The container 10 shown in FIG. 1 includes a box 30 which is installed on the dispenser by pressing the box down through the open top 14 of the dispenser, until stops 32 on the box lie a small distance above the walls 14w of the open top. At that time, a release device 34 of the container will lie within an opening 36 of the dispenser, with the bottom 38 of the box lying substantially at the bottom of the dispenser opening 36. An outer end 40 of the release device forms a handle that can be pulled out, which allows a bottom wall of the box to open and the earplugs to drop out into the dispenser hopper.

As shown in FIG. 2, the box has four sides or side walls 41–44, a top or top wall 46, and a bottom or bottom wall 48. The box forms an earplug-holding volume 49 in the space above the bottom wall 48 and within at least lower portions of the sidewalls 41–44. The handle 40 of the release device is horizontally spaced from the earplug-holding volume 49 and from an imaginary downward extension of the volume 49, to enable the handle to be grasped when the box lies within the dispenser. The bottom wall includes first and second flaps 50, 52. As shown in FIG. 3, each flap has an inner end 54, 56 pivotally mounted on the lower edge 60, 62 of corresponding opposite side walls 41, 42. The lower edges are laterally spaced, each flap also has an outer flap portion 64, 66. The release device 34 has an inner part 70 coupled to the outer flap portions 64, 66 to support each flap portion from moving down. When the release device handle 40 is pulled out in the direction of arrow A, the flap outer portions are released to pivot down. The flaps pivot down under the weight of the articles contained in the box, and because of a tendency of the box to return to an unfolded configuration.

As shown in FIG. 6, each of the flaps has a main part 72, 74 both lying in a substantially horizontal plane. Each flap outer portion includes a largely vertical tab 76, 78 which is engaged with the release device 34. Each tab has a slot 80, 82 with an upper slot wall forming a downwardly-facing surface or shoulder 84. The release device is preferably in the form of a rigid plate of material such as cardboard. The release device has a middle portion 86 with locations that bear against the shoulders 84 of the tabs, and has opposite sides 90, 92 that bear against upper surfaces 94, 96 of the flap main parts 72, 74.

As shown in FIG. 5, the middle portion 86 of the substantially rigid plate-like release device 34 presses up against the shoulders 84 of the tabs 76, 78. At the same time, the opposite sides 90, 92 of the release device press down against the upper surfaces 94, 96 of the flap main parts 72, 74. The sides 90, 92 are laterally spaced from the shoulders. As the flaps 50, 52 begin to pivot downwardly, the tabs 76, 78 and the middle 86 of the release device, tend to move down much further than the opposite sides 90, 92 of the release device. As a result, the opposite sides 90, 92 of the release device are supported on the flaps, and the middle 86 of the release device supports the tabs 76, 78 and therefore the outer end portions of the flaps. Thus, the release device prevents the outer portions of the flaps from moving down by more than a small amount, to thereby prevent release of the articles in the box. When the release device 34 is pulled out, the flaps are free to move down and release the articles. Applicant prefers to construct the release device so its maximum width C (FIG. 3) where it engages the upper surfaces of the flaps, is at least 20 percent of the width D of each of the flaps, and preferably is at least 40 percent of the width of the flaps.

Referring again to FIG. 6, it can be seen that the release device 34 has a slot 100 which receives the two tabs 76, 78. This prevents more than small movement of the release device, except in outward and inward directions A, B.

As shown in FIG. 1, the box 30 has horizontal dimensions only slightly less than the top opening in the container at 14. Applicant originally formed the frame with a cross wall indicated at 102 above the opening 36. This required the handle 40 of the release device to bend up as the box was installed. Applicant now avoids the cross wall 102, in order to make box installation easier. The opening 36 includes a lower part 104 whose width allows it to closely receive the release device handle 40, to minimize gaps through which earplugs might escape. Initially, the box is supported by abutment of the handle 40 with an upwardly facing frame shoulder 106 at the bottom of the opening lower part 104. After the release device is pulled out, the box can move down a small distance such as 5 mm until the stops 32 abut the top wall 14. Because of considerable tolerances in manufacture of the boxes, if the box has to initially rest on the stops 32, then there may be a gap between the handle 40 and the bottom 106 of the frame opening through which earplugs might escape.

Figure 7:
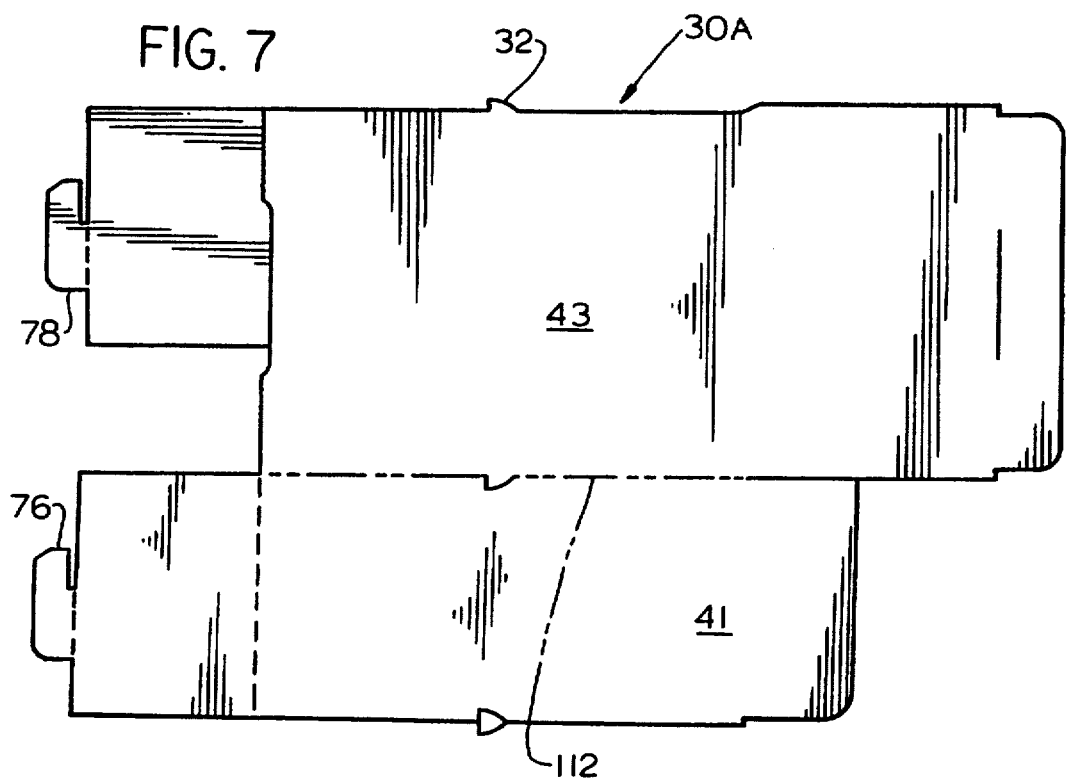
FIG. 7 is a front elevation view of the box of FIG. 3, shown constructed and ready for shipment to an earplug manufacturer, but prior to unfolding of the box.
Figure 8:
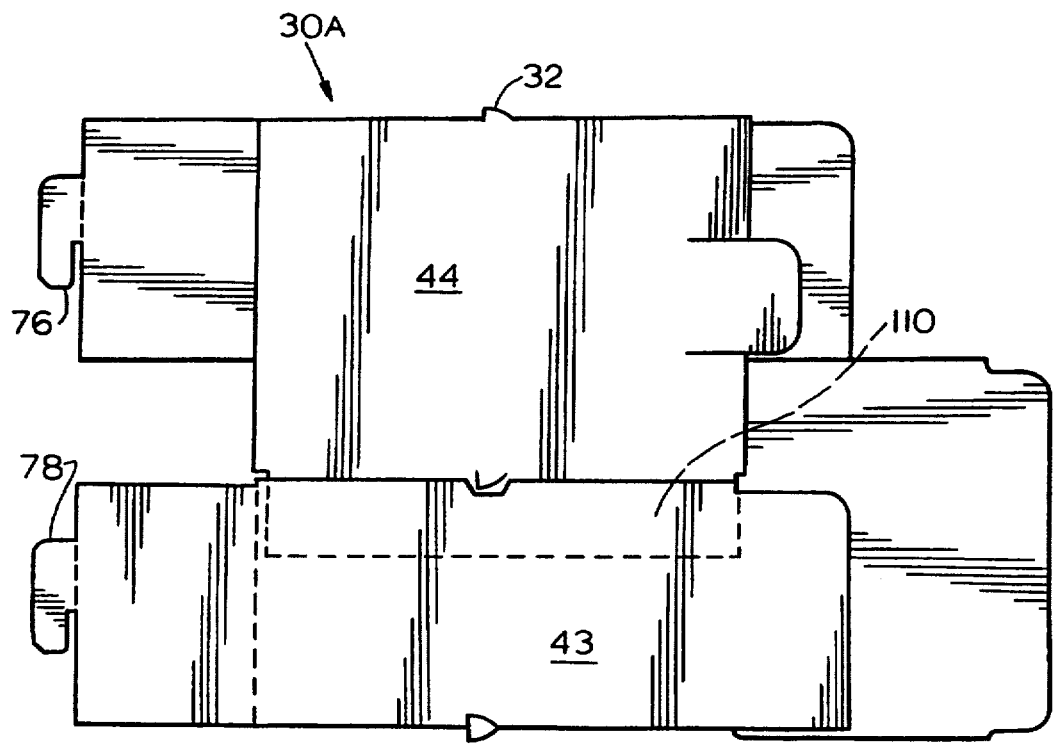
FIG. 8 is a rear elevation view of a box in the configuration of FIG. 7.

FIGS. 7 and 8 illustrate the box at 30A in its manufactured but flat orientation, in which it is shipped to the earplug manufacturer for filling up with earplugs. The box is formed from a single sheet of cardboard which has been bent as shown, and with the ends of the single sheet overlapping at 110 in FIG. 8. The stops 32 are formed by cuts along the corners such as at 112 where a pair of adjacent side walls meet. When the box is folded to its use position for fill up with earplugs, all of the stops 32 project and leave small holes in the box. However, the stops 32 are much smaller than the earplugs, so there is no danger that the earplugs will fall out. If much smaller articles are to be held, then stops can be formed by attaching separate pieces of cardboard to the outside walls of the container. The release device 34 (FIG. 3) also can be formed of a sheet of cardboard.

Applicant prefers to construct the release device 34 (FIG. 6) so its inner end 114 substantially abuts the outwardly facing surface 116 of the rear or innermost box side wall 44, across the width of the release device. The release device thereby couples the bottom wall flaps 50, 52 to the rear wall 44. This enables the release device to help keep the bottom of the rear wall extending parallel to the inner edges 118 of the flaps, to avoid a gap through which earplugs could escape.

Applicant has constructed and successfully tested containers of the configuration shown in FIGS. 1–8. Each box was of cardboard of 3/16ths inch (2.5 mm) thickness. Each flap (FIG. 3) had a width D of 3.25 inches(8.4 cm) and depth of 4.5 inches (11.5 cm). The release device had a width C of 3 inches (7.6 cm). The other dimensions relative to those given above are as shown in the drawings, particularly FIGS. 7 and 8.

Figure 9:
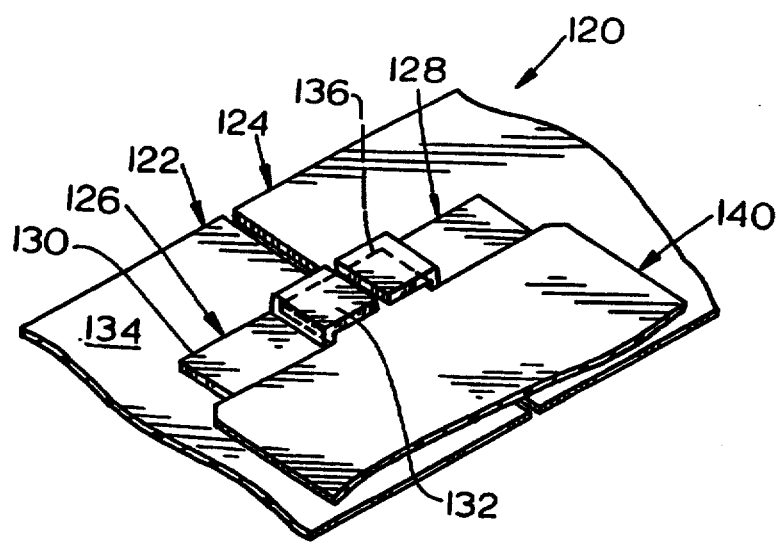
FIG. 9 is a partial isometric view of a container constructed in accordance with another embodiment of the invention.

FIG. 9 illustrates a portion of another container 120 which includes a pair of flaps 122, 124 forming much of its bottom wall. However, instead of forming the flaps with upstanding tabs as extensions of the outer edges of the flaps, the tabs are in the form of separate rigid tabs 126, 128 having inner parts 130 fastened as by adhesive or staples to the corresponding flaps 122, 124. Each tab also has an upstanding portion 132 slightly spaced from an upper surface 134 of a corresponding flap to receive an inner portion 136 of a release device 140. The particular tabs 126, 128 can be formed of rigid plastic. The release device will act in the same manner as for the embodiment of FIGS. 1–8 to prevent the flaps from pivoting down until the release device is pulled out.

Figure 10:
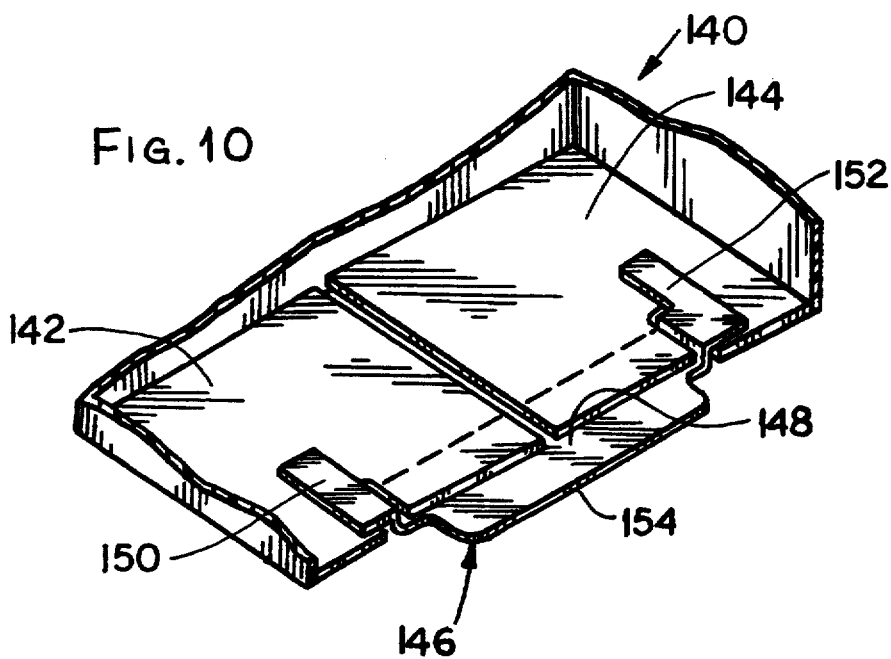
FIG. 10 is a partial isometric view of a container of another embodiment of the invention.

FIG. 10 illustrates a portion of another container 140 which includes a pair of flaps 142, 144 forming much of its bottom wall. However, a release device 146 has a middle 148 which lies under the flaps and opposite ends 150, 152 that lie over the flaps. The handle 154 is shown cutaway at its ends, to aid in the illustration.

Figure 11:
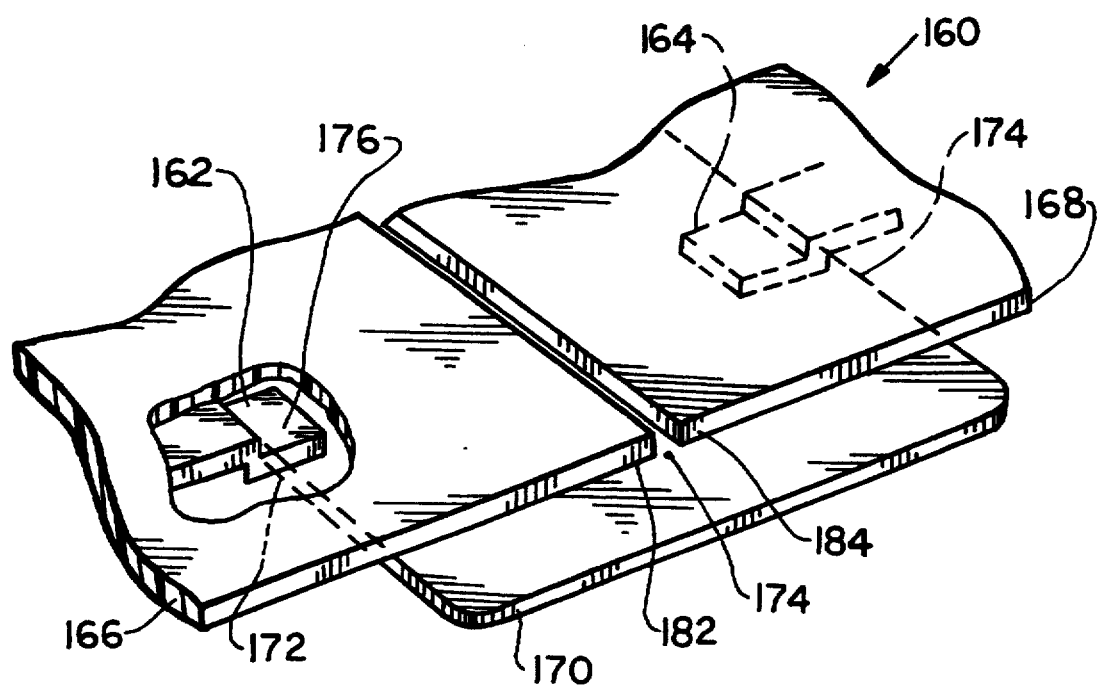
FIG. 11 is a partial isometric view of a container of another embodiment of the invention.

FIG. 11 illustrates a portion of another container 160 which includes a pair of tabs 162, 164 lying below the bottom surfaces of the flaps 166, 168. A release device 170 in the form of a plate lies under the flaps. The release device has an inner end with opposite sides 172, 174 captured in the tabs and abutting vertically-facing shoulders 176 of the tabs. The middle 180 of the release device abuts the outer flap portions 182, 184.

Although applicant prefers to use two separate flaps, it is possible to use a single flap which may extend across the entire open bottom of a container. In that case, the outer end of the flap can be held by a release device to another part of the container such as a side wall, to prevent pivoting down of the flap until the release device is at least partially removed.

It is noted that applicant has tried several different techniques to enable a box to be installed in a dispenser and earplugs in the box then to be released. One approach was to use a vinyl plastic sheet covering the bottom of the box, and upstanding blades on the dispenser, to cut three sides of the vinyl cover when the box was pushed hard down into the dispenser. However, the presence of the upstanding sharp-pointed blades, resulted in the possibility of harm to workers. An approach related to the present one, that applicant tried, was to use a pair of flaps at the bottom of the box, but to use a piece of folded-over tape which could be pulled to peel the tape from the flaps and allow them to pivot down. Applicant's present approach has been found to assure reliable release of the flaps and closure of the box in a low cost construction.

While terms such as "horizontal", "vertical", etc. are used herein to describe the invention, it should be understood that the box can be transported in any orientation with respect to gravity, and preferably is transported and stored with its bottom wall largely uppermost. However, it is preferred that the bottom wall face at least partially downwardly when the release device is pulled to release the contents of the container. Although applicant has developed the container to hold earplugs, it is possible for the container to be used to hold other articles of moderately small size, as described above.

Thus, the invention provides a container which can hold multiple small articles, especially earplugs, and which can be inserted into an open top portion of a dispenser or other receiver, where the box can be readily released to allow the articles to fall out. The box has a bottom wall forming at least one flap, and a release device is provided which has an inner end which holds an outer portion of the flap to another portion of the box. When the release device is moved to a release position, as by purling it, the flap is released to pivot down. The bottom wall preferably includes two flaps, each having an upstanding tab at its outer portion. The release device has a middle portion which lies under shoulders of the tabs, and has widely spaced opposite sides which bear against upper surfaces of the flaps. It is possible to locate the release device under the bottom wall flaps, and it is possible to use more than two flaps such as three of them which are all held by the release device although applicant prefers to use two flaps.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. A container which can hold multiple earplugs and which can be inserted into an open top portion of an earplug dispenser where the container can be readily opened to allow the earplugs to fall into the dispenser, which includes a box having side walls and a bottom wall and forming an earplug-holding volume above said bottom wall and within lower portions of said side walls, with a first of said side walls having a lower edge, said bottom wall including at least a first flap having an inner end pivotably mounted on said lower edge of said first of said side walls and having an outer flap portion, characterized by:

a release device having an inner part coupled to said outer flap portion and to another part of said box to support said outer flap portion from moving down, said release device having an outer release device part forming a handle which can be pulled outwardly to decouple said inner part of said release device from said outer flap portion and allow said flap to pivot down;

said handle being positioned so when said bottom wall lies directly below said earplug-holding volume, said handle is largely horizontally spaced from said bottom wall so said handle does not lie under said bottom wall.

2. The container described in claim 1 wherein:

a second of said side walls lies opposite said first side wall and has a lower edge;

said bottom wall includes a second flap having an inner end pivotally mounted on said second side wall lower edge and having an outer second flap portion forming said another part of said box;

said release device inner part being coupled to said outer flap portions to prevent said flap outer portions from separating and therefore prevent their downward pivoting, until said release device is pulled.

3. The container described in claim 1 including:

an earplug dispenser which has a frame with a box-receiving open upper part constructed with walls that closely receive said box, said walls including a first wall with an opening through which said handle projects to a position outside said frame, to enable grasping and pulling of said handle.

4. The container described in claim 3 wherein:

said frame forms a shoulder at the bottom of said opening;

said box is constructed so said handle of said release device can abut said shoulder and support said box when said box is initially installed in said box-receiving open upper part.

5. A container which can hold multiple articles and which can be rapidly opened, comprising:

a box having at least side and bottom walls, said side walls including largely opposite and laterally spaced first and second side walls having lower edges, and said bottom wall including first and second flaps having upper and lower surfaces, said flaps having inner ends pivotally mounted on corresponding ones of said side wall edges and having adjacent outer end portions, with each flap having a tab forming a largely vertically-facing shoulder that faces in a first vertical direction, and with each flap having a flap location that faces substantially in a second vertical direction that is opposite to said first vertical direction;

a release device having an inner portion with a first face that includes first locations engaging said shoulders, and with an opposite second face having second locations that are laterally spaced from said first locations and that engage said flap locations, said release device being slidable to remove said inner portion from said tabs to allow said flaps to pivot down.

6. An earplug container which can hold multiple earplugs and which can be rapidly opened after insertion into an open top of an earplug dispenser, comprising:

a box having four side walls forming a rectangular opening therewithin, and having a bottom comprising first and second flaps with adjacent outer ends and with inner ends pivotally mounted on lower ends of opposite of said side walls;

each of said flaps having an upper surface and each of said flap outer ends having an upstanding tab with a slot, each slot having an upper slot wall;

a release device largely in the form of a plate with a middle lying in said slots and abutting said upper slot walls and with opposite sides abutting upper surfaces of said flaps.

7. The combination of an earplug dispenser having a frame with a hopper for receiving earplugs and having a mechanism for dispensing the earplugs, and a container for loading earplugs into said frame, wherein:

said frame has a box-receiving upper part with a top, said upper part lying above said hopper and said box-receiving upper part having four primarily vertically-extending side walls forming a substantially rectangular opening, with a first of said side walls having an opening lying at substantially the bottom of said box-receiving upper part;

said container includes an earplug box for holding a multiplicity of earplugs, said box having four side walls with lower portions that fit closely in said box-receiving upper part of said frame, said box having a lower end with at least one flap having an inner edge pivotally mounted on one of said side walls and having an opposite outer edge;

said flap being pivotable from a closed position wherein it closes said box lower end, to an open position wherein said outer edge moves down to open said box lower end and allow earplugs in said box to fall into said hopper;

said container includes a release device which holds said flap outer edge to another portion of said box to prevent pivoting of said flap, but with said release device capable of being pulled to stop holding said flap outer edge to said another portion, said release device having a handle which projects out of said frame opening when said box is installed in said frame, to enable a person to grasp and pull said handle and allow said flap to pivot to said open position so said earplugs can fall into said hopper.

8. The combination described in claim 7 wherein:

said frame opening has a bottom forming an upward-facing shoulder, and said box lies in said frame upper part with said handle resting on said shoulder.

9. A method for holding and then releasing earplugs into a dispenser that has an open top, comprising:

forming a box with side walls and a bottom wall, including forming said bottom wall with a pair of flaps that have upper and lower flap surfaces, and that each have inner ends pivotally mounted on opposite side walls and adjacent outer ends, including forming each of said outer ends with a largely vertically-facing shoulder lying a vertical distance from a first one of said flap surfaces;

inserting a plate between said shoulders and said first flap surfaces of both of said flaps to thereby prevent said flaps from pivoting down until said plate is removed.

10. A container which can hold multiple earplugs and which can be inserted into an open top portion of an earplug dispenser where the container can be readily opened to allow the earplugs to fall into the dispenser, which includes a box having side walls and a bottom wall, with first and second of said side walls lying opposite each other and each having a lower edge, said bottom wall including first and second flaps each having an inner end pivotably mounted on a corresponding one of said lower edges and each having an outer flap portion, characterized by:

a release device having an inner part coupled to said outer flap portions to support said outer flap portions from moving down, said release device having an outer release device part forming a handle which can be pulled outwardly to decouple said inner part of said release device from said outer flap portions and allow said flaps to pivot down;

said flaps each have a main part lying in a substantially horizontal plane and said outer portions each have a tab, and each tab has a slot with an upper slot wall forming a largely downwardly-facing surface;

said release device inner part is slidably received in said slots, so as said release device handle is pulled outwardly said release device moves out of said slots.

11. The container described in claim 10 wherein:

said release device is in the form of a rigid plate having a width that is at least 20 percent of the width of each of said flaps, said plate having opposite sides that bear against upper surfaces of said flaps, and said plate having a middle that bears against said downwardly facing surfaces of said tabs.

12. A container which can hold multiple earplugs and which can be inserted into an open top portion of an earplug dispenser where the [box]container can be readily opened to allow the earplugs to fall into the dispenser, which includes a box having side walls and a bottom wall, with first and second of said side walls lying opposite each other and each having a lower edge, said bottom wall including first and second flaps each having an inner end pivotably mounted on a corresponding one of said lower edges and each having an outer flap portion, characterized by:

a release device having an inner part coupled to said outer flap portions to support said outer flap portions from moving down, said release device having an outer release device part forming a handle which can be pulled outwardly to decouple said inner part of said release device from said outer flap portions and allow said flaps to pivot down;

said box side walls include an innermost side wall lying opposite said release device handle and having an outwardly facing surface, and said flaps have upper surfaces and have inner edges lying adjacent to said innermost side wall;

said release device comprises a rigid plate having opposite sides bearing against said upper surfaces of said flaps and a middle engaged with said flap outer portions;

said plate having an inner end which substantially abuts said innermost side wall to keep its outwardly facing surface substantially parallel to said flap inner edges.

13. A container which can hold multiple earplugs and which can be inserted into an open top portion of an earplug dispenser where the container can be readily opened to allow the earplugs to fall into the dispenser, which includes a box having side walls and a bottom wall, with first and second of said side walls each having a lower edge, said bottom wall including first and second flaps each having an inner end pivotably mounted on a corresponding one of said lower edges and each having an outer flap portion, characterized by:

a release device having an inner part coupled to said outer flap portions to support said outer flap portions from moving down, said release device having an outer release device part forming a handle which can be pulled outwardly to decouple said inner part of said release device from said outer flap portions and allow said flaps to pivot down;

said outer flap portions each have an upstanding tab with a slot forming a downwardly-facing shoulder, with said flaps each having an upper surface;

said release device inner part has a middle lying against said shoulders and has opposite sides lying against locations on said flap upper surfaces beyond opposite sides of said tab shoulders;

said release device location is constructed to slide out of said slots when said handle is pulled outwardly.

14. A container which can hold multiple earplugs and which can be rapidly opened, comprising:

a box having at least side and bottom walls, said side walls including largely opposite first and second side walls having lower edges, and said bottom wall including first and second flaps having upper and lower surfaces, said flaps having inner ends pivotally mounted on corresponding ones of said side wall edges and having adjacent outer end portions, with each flap having a tab forming a largely vertically-facing shoulder;

a release device having an inner portion with a first face that includes locations engaging said shoulders, and with an opposite second face having locations engaging said flaps, said release device being slidable to remove said inner portion from said tabs to allow said flaps to pivot down;

each of said flaps has a largely horizontal main portion and has an outer edge forming one of said tabs which is bent about 90° from the main portion to extend largely vertically, with each tab having a horizontal slot that includes a slot wall forming one of said shoulders, with said release device inner portion lying in said slots.

15. A container which can hold multiple earplugs and which can be rapidly opened, comprising:

a box having at least side and bottom walls, said side walls including largely opposite first and second side walls having lower edges, and said bottom wall including first and second flaps having upper and lower surfaces, said flaps having inner ends pivotally mounted on corresponding ones of said side wall edges and having adjacent outer end portions, with each flap having a tab forming a largely vertically-facing shoulder;

a release device having an inner portion with a first face that includes locations engaging said shoulders, and with an opposite second face having locations engaging said flaps, said release device being slidable to remove said inner portion from said tabs to allow said flaps to pivot down;

said box is formed of a single sheet of cardboard, said box forming four of said side walls with adjacent side walls each joined along a vertical corner, with each of a plurality of said side walls forming a projection extending beyond a corresponding corner and forming a downwardly-facing shoulder for abutting a top wall of a device which receives said box.

* * * * *